United States Patent [19]

Senftle et al.

[11] Patent Number: 5,352,412
[45] Date of Patent: Oct. 4, 1994

[54] APPARATUS FOR GENERATING PYROLYZATES OF MICROSCOPIC PARTICLES

[75] Inventors: Joseph T. Senftle; Richard L. Tharp, both of Plano, Tex.

[73] Assignee: Atlantic Richfield Company, Los Angeles, Calif.

[21] Appl. No.: 22,701

[22] Filed: Mar. 1, 1993

[51] Int. Cl.$^5$ .................... G01N 25/02; G01N 33/24
[52] U.S. Cl. ...................... 422/78; 356/318; 422/80; 422/82.05; 436/25; 436/32; 436/155
[58] Field of Search .................... 422/78, 80, 82.05; 436/25, 32, 155, 181; 356/317, 318

[56] References Cited

U.S. PATENT DOCUMENTS 5,075,552 12/1991 McClelland et al. .............. 250/341
5,147,611 9/1992 Stout et al. ..................... 422/78

Primary Examiner—Jill A. Johnston
Attorney, Agent, or Firm—Michael E. Martin

[57] ABSTRACT

An optical microscope supports a housing having a closed chamber in which a particle to be pyrolyzed is disposed and is exposable to a targeting laser beam for precisely positioning the particle and a power laser beam for heating and pyrolyzing the selected particle. The pyrolysis chamber housing is supported on a heater disposed on the microscope stage for movement into the focal plane of the objective lens and into the beam path of the targeting and power lasers. The lasers are mounted together and, in combination with multiple reflecting mirrors, direct their beams along a common beam path. The lasers are mounted on an adjustable support base for adjusting the position of the beam path along three mutually perpendicular axes.

19 Claims, 2 Drawing Sheets

APPARATUS FOR GENERATING PYROLYZATES OF MICROSCOPIC PARTICLES

BACKGROUND OF THE INVENTION

1. Field of the Invention

The present invention pertains to an apparatus for the pyrolysis of microscopic particles by isolating a composite sample in a closed chamber and heating the sample with a concentrated energy source such as a laser while specifically targeting a predetermined minute particle of matter within the sample.

2. Background

Certain devices have been developed for the analysis of the chemical or physical properties of materials which are found in heterogeneous composite structures. One field of endeavor in which it is desirable to identify the chemical and physical properties of a particular material is in exploration for hydrocarbon sources wherein it is desirable to analyze the composition of source rocks and, in particular, to analyze a particular material which is embedded in or comprises part of the source rock in small quantities.

U.S. Pat. No. 5,147,611, issued Sep. 15, 1992 to S. A. Stout, et al, describes a device which includes a microscope for optically examining and positioning a heterogeneous composite sample. The microscope is operated in combination with targeting and heating laser light sources to generate pyrolyzates of specific materials in the sample. Although the device described in the Stout et al patent includes certain improvements over prior art methods and apparatus for examining and determining the properties of geological, biological and man-made materials, certain problems remain to be solved in the development of such devices or systems. The present invention addresses some of these problems and the apparatus of the present invention overcomes certain problems associated with prior art apparatus as well as providing other improvements in apparatus for targeting microscopic particles in a composite sample and generating pyrolyzates of such particles.

SUMMARY OF THE INVENTION

The present invention provides an improved apparatus for targeting microscopic size particles in a sample of heterogeneous material and for generating pyrolyzates of selected ones of the particles.

In accordance with one aspect of the present invention, a particle-targeting and pyrolyzate-generating apparatus is provided wherein a closable chamber is formed by a housing which includes an optical viewing window and a window for admitting a heat source such as a laser beam to the chamber, the housing being supportable on a movable stage for optimum positioning with respect to the optical structure, such as a microscope, and with respect to a source of positioning or targeting laser light and a heat-generating laser source. The housing includes a removable cover for supporting a sample of material to be targeted and pyrolyzed and the chamber is operable to be connected to a source of purge and transport fluid and to a pyrolyzate analysis device for removing the pyrolyzed material from the chamber. Different samples of material to be optically examined and targeted for generating pyrolyzates may be inserted in and removed from the chamber without moving the housing with respect to the focal plane of the optical structure such as a microscope objective lens.

In accordance with another aspect of the present invention, an improved microscope or optical viewing structure is provided for use in generating pyrolyzates of microscopic particles wherein the support stage for the microscope is operable to support a heater on which a housing is disposed and includes a chamber for containing the sample to be pyrolyzed and further wherein the stage is operable to be moved only a limited amount with respect to the optical viewing axis and the laser-targeting axis.

In accordance with yet another aspect of the present invention, a unique arrangement of a targeting light beam source and a heat-generating beam source is provided which is compact, has a common beam axis for the targeting beam and the heat-generating beam and includes a compact and unique arrangement of beam guiding and shielding structure. The beam guiding and shielding structure is also adapted to provide improved beam focusing and collimating means. The support structure for the targeting beam and heat-generating beam sources and the support structure for the target are both operable to provide greater flexibility in positioning the targeting beam and heat-generating beam sources as well as positioning the target with respect to the beam sources and with respect to optical devices required for viewing the sample of material to be targeted and have a certain portion thereof pyrolyzed.

Those skilled in the art will recognize the above-mentioned advantages and superior features of the present invention together with other important aspects thereof upon reading the detailed description which follows in conjunction with the drawing.

BRIEF DESCRIPTION OF THE DRAWING

FIG. 6 is a detail section view taken generally from the line 6—6 of FIG. 1.

DESCRIPTION OF A PREFERRED EMBODIMENT

Figure 1:
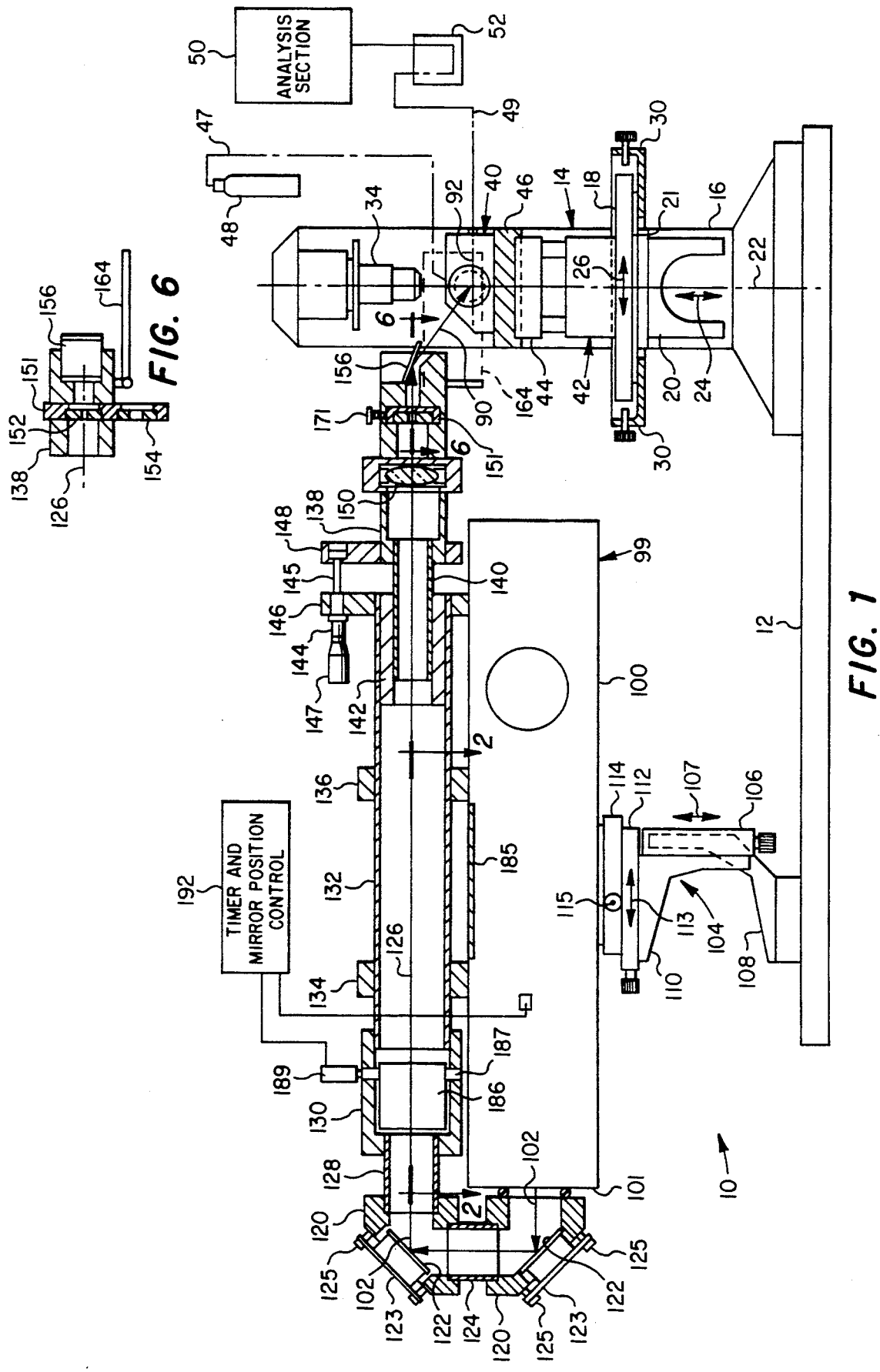
FIG. 1 is a side elevation, partially sectioned, of the apparatus of the present invention.

In the description which follows, like parts are marked throughout the specification and drawing with the same reference numerals, respectively. The drawing figures are not necessarily to scale and certain elements are shown in somewhat generalized or schematic form in the interest of clarity and conciseness.

Referring to FIG. 1, the improved pyrolyzate-generating apparatus of the present invention is illustrated and generally designated by the numeral 10. The apparatus 10 includes two major components to be described hereinbelow and which are both supported on a substructure or support base 12. One of the major components of the apparatus 10 comprises an optical microscope 14 having a support frame 16 on which is supported a movable stage 18 of generally conventional construction. The stage 18 is operably supported on the frame 16 by a vertically-movable support bracket 20 which is operable to move parallel to an optical axis 22 in the directions of the double-ended arrow 24. The support stage 18 is also operable to move in a conventional manner with respect to the bracket 20 along mutually-perpendicular axes which lie in a plane normal to the axis 22. Double-ended arrows 26 and 28, see FIG. 3, indicate the direction of movement of the stage 18 in the aforementioned plane which is normal to the axis 22. Conventional mechanism, not shown, and known to those skilled in the art of optical microscopes is operable to move the stage 18 in the directions indicated by the arrows 24, 26 and 28. The stage 18 is supported on a sub-bracket 21 interposed between the stage and the bracket 20 whereby the stage 18 is movable in the directions of the arrows 26 and 28 with respect to the bracket 20 and the sub-bracket 21.

Figure 3:
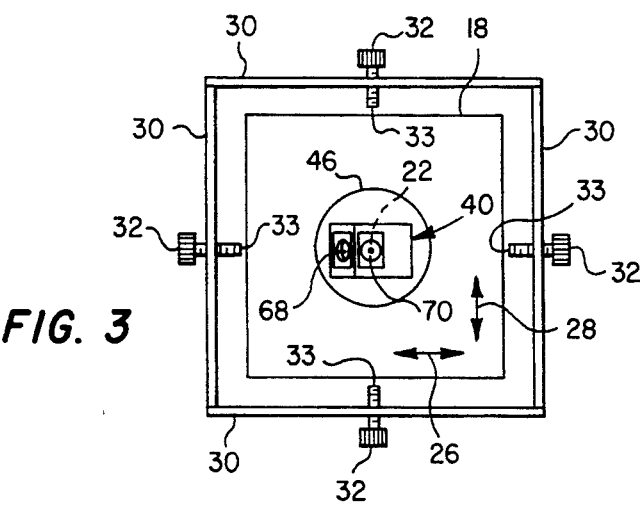
FIG. 3 is a plan view of the microscope stage showing the stage movement limiting structure.

In accordance with the present invention, an improved arrangement of a stage movement limiting structure is provided wherein opposed support plates 30 formed in a generally square configuration, see FIG. 3, are supported on and by the sub-bracket 21 whereby the stage 18 is movable in the directions of the arrows 26 and 28 with respect to the plates 30. The plates 30 may be formed of conventional right-angle or L structural shapes. Each of the plates 30 includes a suitable adjusting screw 32 supported thereon and threadedly engaged therewith. The distal ends 33 of the adjusting screws 32 are adapted to engage the sides of the stage 18 to limit the movement of the stage in the directions indicated by the arrows 26 and 28 and with respect to the optical axis 22.

The microscope 14 includes an objective lens system 34, FIG. 1, arranged in a conventional manner for viewing an object supported by the stage 18. The ocular lens system of the microscope 18 has been omitted from drawing FIG. 1 in the interest of clarity. The microscope 14 is preferably of a type used for examining metallurgical specimens and has a vertical illuminator, not shown, which projects light through the objective lens system 34 onto the object to be examined.

In the system 10 a microscopic particle examining and pyrolyzate-generating housing is disposed on the microscope and generally designated by the numeral 40. The housing 40 is supported on the stage 18 by a heating apparatus, generally designated by the numeral 42. The heating apparatus 42 may be a conventional resistance type heater having a generally cylindrical shaped heating element 44. A heat sink member 46 is supported on the heating element 44 and preferably comprises a solid metal or ceramic block which directly supports the housing 40 and provides a stable heat source for uniform heating of the housing 40. The heating apparatus 42 may be a conventional laboratory heater or hot plate which is electrically energized and adapted to provide heat at a substantially constant temperature setting. The heater 42 may be of a type commercially available such as a Thermodyne 2300 Hot Plate. It is preferred to heat the housing 40 for examining specimens which are believed to include hydrocarbon substances to a temperature of about 250° C. to 275° C.

As shown in FIG. 1, the housing 40 is adapted to be connected to a source 48 of purge and transport gas for purging a chamber formed in the housing to be described in further detail herein. The housing 40 is also operably connected to a pyrolyzate analysis device or system, generally designated by the numeral 50 which may include suitable chromatography or spectrographic analysis equipment. A cold trap or condenser 52 is interposed between the analysis device or section 50 and the housing 40. Conduits 47 and 49 interconnect the housing 40 with the source of purge gas 48 and the condenser or cold trap 52, respectively.

Figure 4:
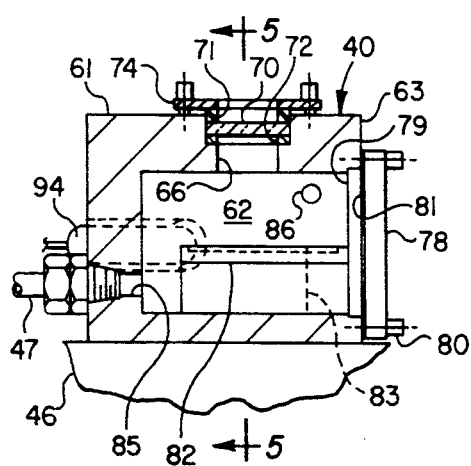
FIG. 4 is a detail section view of the sample support housing, taken generally from the line 4—4 of FIG. 5.
Figure 5:
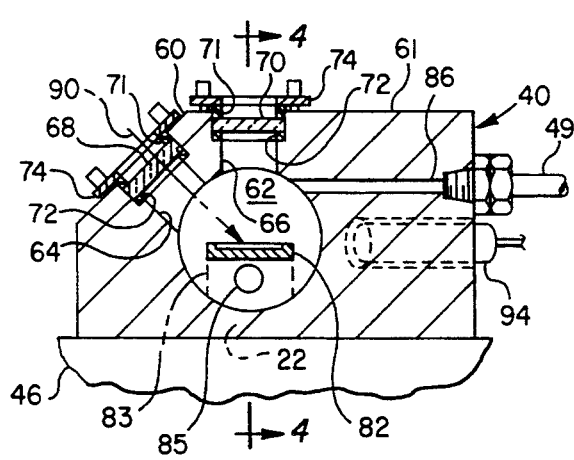
FIG. 5 is a section view taken generally from the line 5—5 of FIG. 4.

Referring now to FIGS. 4 and 5, in particular, the housing 40 comprises a generally rectangular block, preferably made of stainless steel or a similar conductive and corrosion resistant metal and which is suitably supported on and secured to the heat sink 46. The housing 40 has a scarfed face 60, as shown in FIG. 5, between its top side and one transverse end of the housing. A generally cylindrical chamber 62 is formed in the housing 40 and is intersected by generally cylindrical bores 64 and 66 which, respectively, are closed by transparent windows 68 and 70. The window 68 is preferably formed of zinc selenide to allow relatively long wavelength, infrared radiation to pass through the window and into the chamber 62. The window 70 is preferably formed of quartz to readily pass visible light rays therethrough with respect to the chamber 62. The windows 68 and 70 are both secured in counter-bore portions of the bores 64 and 66 between resilient cushion rings 71 and graphite seal rings 72 by removable covers 74 which are each suitably fastened to the face 60 and the top side 61, respectively, of the housing 40. The cushion rings 71 are preferably formed of silicone rubber and are operable to allow thermal expansion of the windows 68 and 70 and the seal rings 72 without cracking the windows. The covers 74 each include a central bore therethrough to permit visible and near infrared radiation to pass readily through the windows 70 and 68.

The chamber 62 opens to one longitudinal side 63 of the housing 40 and is closed by a removable cover 78 which is suitably secured to the housing 40 by conventional threaded fasteners 80. A copper seal ring 81 is interposed between the cover 78 and the face 63. The cover 78 may have a generally cylindrical pilot portion 79 for precisely locating the cover with respect to the chamber 62 and, in particular, a support member 82 which is formed as part of the cover within the chamber as illustrated in FIGS. 4 and 5. Alternatively, the support member 82 may have its own support or base portion 83 for disposal within the chamber 62 even when the cover 78 is removed or the support member may be defined by the chamber wall. The support member 82 is operable to support a sample of material, not shown, to be operated on by the apparatus 10 in a manner to be described in further detail herein. Purge gas may be admitted to the chamber 62 by way of the conduit 47 and a passage 85 and evacuated from the chamber through a passage 86, FIG. 5, which is in communication with the conduit 49. The passage 86 is spaced apart from and above the passage 85, with the support member 82 interposed therebetween, so that the pyrolyzate vapor is more effectively swept out of the chamber 62.

The operation of the apparatus 10 is one wherein, basically, a sample of material containing microscopic particles that are to be pyrolyzed and analyzed by the apparatus is supported on the support member 82 in a position such that substantially all of the sample may be viewed through the microscope 14 and the window 70 while the precise location of the particle to be pyrolyzed is positioned with respect to a beam centerline 90, FIGS. 1 and 5, so that a near infrared electromagnetic radiation beam may be focused on the particle along the beam centerline 90 to pyrolyze the particle. The pyrolyzate generated by such action is then swept out of the chamber 62 through the passage 86 and the conduit 49 by a suitable inert purge and transport gas from the source 48. Thanks to the arrangement of the housing 40 with its closed chamber 62, viewing window 70 and beam transmitting window 68, a sample to be pyrolyzed may be located precisely by positioning the housing so that the particle to be pyrolyzed lies in the focal plane 92, FIG. 1, of the microscope 14 and is then also aligned with the beam centerline 90 so that a concentrated beam of electromagnetic radiation may be brought to bear on the particle to be pyrolyzed to generate the pyrolyzate of such particle. The temperature in the chamber 62 may be constantly monitored by a suitable thermocouple or other temperature indicator 94, FIG. 4, disposed in the housing 40 in proximity to the chamber 62. Further, thanks to the provision of the housing 40, which is supported on the microscope stage 18 and not connected to the objective lens system 34, such housing may be moved to place a material sample supported on the support member 82 in the focal plane 92 and also to target the particle to be pyrolyzed by a beam directed along the beam centerline 90. The cover 78 may be removed and the material sample supported on the support member 82 replaced by another sample and the cover replaced without disturbing the working position of the support member with respect to the focal plane 92. In this way, a substantial amount of time required to refocus the objective lens on the particle to be targeted for pyrolysis is eliminated. Moreover, greater flexibility in utilizing the objective lens with regard to optically viewing certain samples in the chamber 62 is provided by the arrangement of the housing 40. Still further, the chamber 62 is reliably maintained in a sealed or hermetically tight condition so that the pyrolyzate is not contaminated or escape the chamber during the measurement process.

Figure 2:
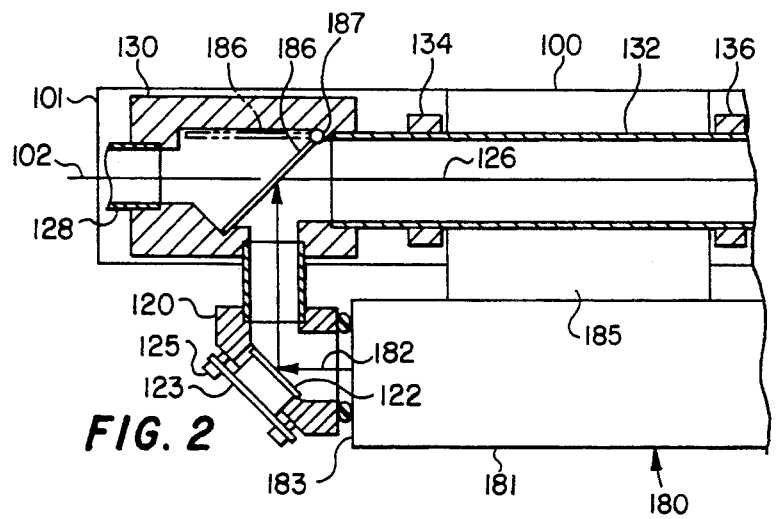
FIG. 2 is a detail section view taken generally along the line 2—2 of FIG. 1.

Referring further to FIGS. 1 and 2, in particular, the other major component of the system or apparatus 10 previously mentioned comprises a source of focused electromagnetic radiation for heating and pyrolyzing the aforementioned microscopic particles which includes means for focusing and restricting the intensity of a radiation beam as well as improved means for aiming or targeting the beam on the desired sample particle. In FIG. 1, there is illustrated an enclosure 100 for a heat source comprising a carbon dioxide laser apparatus 99 which is operable to generate a laser beam 102 emanating from an end portion 101 of the enclosure 100. The enclosure 100 is desirably supported on the base 12 by a triaxial adjusting mechanism, generally designated by the numeral 104 which includes a first micrometer adjustable slide positioner mechanism 106 of a type commercially available which is supported on a support bracket 108 secured to the base 12. A second support bracket 110 interconnects the slide positioner 106 with a second micrometer slide positioner 112 which is operable to adjust the position of the enclosure 100 and structure supported thereby in a direction along an axis indicated by the arrow 113. In like manner, the micrometer slide positioner 106 adjusts the vertical position of the enclosure 100 and structure supported thereby along an axis indicated by the double arrow 107. Lastly, a third micrometer slide positioner 114 is mounted on the slide positioner 112 and is operable to adjust the position of the enclosure 100 and the structure supported thereby along an axis which is normal to the plane of the paper of FIG. 1 and indicated by the numeral 115. Accordingly, precise alignment of a beam of electromagnetic radiation which will follow the centerline 90 as well as be directed through structure to be described herein may be obtained by adjusting the micrometer slide positioners 106, 112 and 114 to position the enclosure along three mutually perpendicular axes indicated at 107, 113 and 115.

As shown in FIG. 1, the beam 102 from the laser apparatus 99 is directed through a first mirror support housing 120 where it is reflected in a direction normal to the initial direction of the beam by a suitable reflecting mirror 122. A beam shield tube 24 connects the first support housing 120 with a second support housing 120 also supporting a second mirror 122 which redirects the beam 102 along a centerline 126 through a second shield tube 128, a housing 130 and shield tube 132 supported on the enclosure 100 by spaced apart support members 134 and 136. The shield tube 132 also supports an adjustable beam focusing lens and restrictor characterized by an enclosure 138 which is connected to a cylindrical shield tube and bearing member 140. The member 140 is slidably journalled in a bearing 142 disposed in the shield tube 132. The enclosure 138 is adapted to be precisely positioned with respect to the beam shielding and guide structure comprising the housings 120, 130 and the shield tube 132 by a micrometer positioning screw 144 which is interconnected between support brackets 146 and 148, whereby the position of a focusing lens 150 disposed in the enclosure 138 may be adjusted to focus the laser beam 102 as well as a targeting beam, to be described below, which also is directed along the centerline 126.

The enclosure 138 also includes a restrictor support member 150 for supporting one or more removable beam restrictors 152 and 154 having selectively sized apertures formed therein. The enclosure 138 further supports a beam directing mirror 156 which redirects the beam 102 from along the centerline 126 to along the centerline 90 into the chamber 62 as described above. An operator beam shield plate 164 is supported on suitable hinge means attached to the enclosure 138 for movement into position in front of the housing 40 to prevent reflection of any high-energy beams off of the housing and toward an operator viewing the housing during operation of the laser 99.

The micrometer positioning screw device 144 includes a stem portion 145 which is connected to the bracket 148 so that, by rotation of the micrometer adjustment knob 147, the position of the lens 150 may be adjusted with respect to the aforementioned structure to focus a beam along the centerline 126. Moreover, the restrictors 152 and 154 may be selectively positioned so that their apertures are aligned with the centerline 126 to restrict the amount of the beam generated by the laser 99 which strikes the mirror 156 and ultimately the target within the chamber 62. The restrictor support member 151 is slidably disposed in a transverse slot formed in the enclosure 138 and may be locked in a predetermined position in the enclosure by a suitable set screw 171.

The intensity of the beam 102 emanating from the laser 99 is too great to be used as a targeting beam while positioning the sample to be pyrolyzed. Accordingly, it is desirable to provide a low-power targeting laser which has a highly visible but low-energy beam which may be directed along the centerlines 126 and 90 into the chamber 62 for targeting the microscopic particle that is to be pyrolyzed by the high-intensity laser beam. In this regard, a second relatively low-power laser is supported on the enclosure 100 as shown in FIG. 2 and generally designated by the numeral 180. The laser 180 is disposed in an enclosure 181 and directs a low-power visible light laser beam 182 from the end 183 of the enclosure 181 into a third mirror support housing 120 for supporting a third laser-reflecting mirror 122. The low-power laser beam 182 is reflected by the third mirror 122 onto a movable mirror 186 supported in the housing 130 and movable to the position shown in FIG. 2 whereby the laser beam 102 is blocked and the laser beam 182 is redirected along the same optical path, that is, along the centerlines 126 and 90. The mirror 186 may be retracted to a position to permit the laser beam 102 to be directed along the centerline 126 as shown by the alternate position of the mirror 186 in FIG. 2. The mirror 186 is suitably mounted on a pivot shaft 187 which is connected to suitable actuator means 189 for moving the mirror between its alternate operating positions. The actuator 189 and the laser 99 may be controlled by a suitable timer and mirror position control circuit generally designated by the numeral 192. The timer and position control circuit 192 is operable to energize the laser 99 for selected periods of time to control the amount of energy beamed toward the sample to be pyrolyzed in the chamber 62 of the housing 40.

The arrangement of the lasers 99 and 180 described hereinabove is particularly advantageous in that such arrangement is compact and the targeting laser beam and the heat-generating laser beam are directed along the same path so that the position of the heat-generating laser beam 102, when it strikes the sample in the housing 40, will be the same as that targeted by the visible light low-energy targeting laser beam 182. Moreover, supporting the laser 180 on the housing for the laser 99 by the support bracket 185 assures that the positions of these two lasers relative to each other will remain unchanged and, moreover, the beam reflecting mirror support means and the beam-shielding structure are all interconnected and supported on the enclosure 100 of the laser 99 together with the housing 181 of the laser 180 so that greater positioning accuracy for the laser beams is obtained. The compact arrangement of the lasers 99 and 180 is enhanced by arranging their housings so that their output beam paths are both initiated in a direction opposite to the direction that they are pointed for final deflection into the chamber 62. The enclosures 100 and 181, being somewhat generally elongated rectangular boxes, are desirably mounted side-by-side and substantially parallel to each other. Thus, by providing the deflecting mirrors 122 and 186, arranged as illustrated and described above, a compact arrangement is provided which may be easily adjusted for focusing a laser beam along the centerline 126, 90 and for positioning the beam with respect to a target comprising a microscopic particle disposed in the chamber 62.

The laser 99 is preferably a relatively high-energy laser of a type commercially available such as manufactured by Synrad, Inc. A preferred laser is a carbon dioxide power laser having a ten watt power output rating which provides a laser beam in the near infrared range of the electromagnetic spectrum. The targeting laser is a commercially available helium-neon laser of about one miliwatt power output capacity which emanates a visible light beam of low power which may be easily viewed when reflected from a target.

In examining relatively small microscopic particles in hydrocarbon source rocks and the like it is desirable to obtain a laser beam spot in the range of about 300 to 500 microns diameter. Initially, the power laser 99 is adjusted by placing a paper target over the aperture of one or the other of the restrictor members 152 and 154 and adjusting the positions of the mirrors 122 while firing repeated pulses from the laser 100 until the laser beam is centered on the target and on the centerline 126. The mirrors 122 are each mounted on a cover 123, each of which is supported on its housing 120 by plural fasteners 125, respectively, and may be moved such as to change the angular positions of the mirrors. When the beam is indicated to be on the centerline 126, 90 the position of the focusing lens 150 is adjusted by the micrometer positioning device 144 until the size of the beam is in a preferred range, that is about 300 to 500 microns diameter at the target position on the sample support member 82. For each incremental movement of the lens 150 which would tend to reposition the centerline 90, the adjustable support system for the laser enclosure 100 is moved in the opposite direction along one of the axes 107, 113 and 115 so that the laser beam is directed along the centerline 90 even though the reflecting mirror 156 may be moved due to movement of the focusing lens 150. In other words if the lens 150 is moved toward the microscope 14, the micrometer slide positioner 112 is moved in the opposite direction to reposition the mirrors so that the beam is directed along the centerlines 126, 90 to the target sample. The laser 99 may be fired repeatedly to obtain the proper size of beam diameter or "spot" on a sample of material that will give a well-defined spot when burned by a very short burst of energy from the laser in about 0.10 seconds burn time, for example, for the power rating of the laser 99 mentioned hereinabove.

Once the laser beam 102 is centered along the centerlines 126 and 90 to the desired target spot on the support member 82, the targeting laser 180 is also adjusted in the same manner by adjusting the position of its mirror 122 so that its beam is directed along the centerlines 126, 90 to the target previously spotted by the laser 100. Of course, the mirror 186 is moved to the position indicated by the solid lines in FIG. 2 when the beam 182 of the target laser 180 is being positioned.

After the lasers 100 and 180 have been aligned to direct their beams along the centerlines 126 and 90 and the beam of the power laser 100 has been suitably focused by adjustment of the focusing lens 150, the beam intensity may also be modified by selecting the aperture size of the restrictor disks 152 and 154 by positioning the restrictor holder 151 so that the selected aperture is centered on the centerline 126. In the process of aligning the laser beams 102 and 182 with the centerlines 126 and 90, the beams have also been directed to a point at which the axis of the objective lens system 34 intersects the focal plane 92. In other words, the centerline 90 preferably intersects the focal plane 92 at the intersection of the axis 22 with the focal plane. During this adjustment process, the housing 40 is positioned so that the passages 64 and 66 are substantially centered or coaxial with the centerlines 90 and the axis 22 and so that the intersection of the axis 22 with the centerline 90 occurs at the surface of the support member 82. If a sample of material disposed on the support member 82 has a particle which is not at the focal point formed by the intersection of the centerline 90, the axis 22 and the focal plane 92, the stage 18 may be adjusted triaxially to position the particle to be pyrolyzed at the afore-mentioned point of intersection. Thanks to the stops provided by the adjusting screws 32 and the screw support plates 30, movement of the stage 18 and the housing 40 will be limited such that the laser beam centerline 90 will not move away from the window 68, nor will the window 70 be moved laterally to a position which would not permit focused observation of the sample by the objective lens system 34. The stage movement limiting mechanism thus minimizes the chance that the powerful laser beam 102 will strike the housing 40 and be reflected in a direction which might be unwanted. In this regard also, during operation of the laser 100 the shield 164 is normally moved to the position shown in FIGS. 1 and 6 to minimize unwanted reflection of the beam in a direction which could be injurious to system operating personnel.

After positioning a sample having a particle to be pyrolyzed using the targeting laser 180 to direct a visible light beam onto the sample supported by the support member 82, and after firing the laser 99 to pyrolyze the targeted particle, the gaseous pyrolyzate so formed is swept out of the chamber 62 by purge gas such as helium or nitrogen introduced from the conduit 47 and swept out of the chamber through the passage 86 and the conduit 49. The conduits 47 and 49 are preferably insulated and heated to a temperature which will prevent condensation of the pyrolyzate in the chamber 62 or in the conduit 49 until it reaches the condenser or cold trap 52, or in case it is desired to immediately transport the pyrolyzate in gaseous form to the particle analysis section 50.

Moreover, by providing the housing 40 having a hermetically sealable chamber 62 which may be accessed readily without moving the housing with respect to the objective lens system 34, different samples of materials to be analyzed may be readily placed in position for viewing, targeting and to be heated by the laser 99 without moving the housing 40. Each new sample of material that is placed on the support member 82 will be required to be moved only a small distance to bring the selected particle to be analyzed into the focal plane 92 and positioned at the intersection of the focal plane with the centerline 90. Accordingly, only initial adjustment of the beams 102 and 182, as described above, is required to be carried out for the system 10.

Certain ones of the components of the system 10 previously described may be obtained from commercial sources and modified to be operable with the system 10 in accordance with the previous discussion. The metallurgical microscope 14, for example, may be of a type commercially available from Mitutoyo Manufacturing Company, Ltd. as their model FS100. The lens system preferably has a magnification power of about 200× to 400×. As mentioned previously, the power laser 100 may be of a type manufactured by Synrad, Inc. and, in particular, a carbon dioxide type power laser having approximately a ten watt power output rating. The helium neon laser 180 may also be of a type commercially available. The mirrors 122, the lens 150 and the mirror 156 nay be of conventional construction and have properties suitable for reflecting high-intensity focused light beams such as laser beams. The mirrors 122 and 156 may, for example, be molybdenum coated for high reflection efficiency. The micrometer slide positioners 106, 112 and 114 may be of a type available from Klinger Scientific, Inc. under the trademark Microcontrole.

The operation of the system 10 will be readily apparent to those skilled in the art from the foregoing description. Although a preferred embodiment of an improved system for pyrolyzate analysis of particles, particularly particles found in certain source rocks for hydrocarbon substances has been described in detail herein, those skilled in the art will recognize that various substitutions and modifications may be made to the invention without departing from the scope and spirit thereof as defined in the appended claims.

What is claimed is:

1. An apparatus for generating a pyrolyzate of a microscopic particle for analysis comprising:
an optical sensor having a focal plane and a movable support stage operable to move along three mutually perpendicular axes;
a housing supported on said stage and including a closable chamber, a first window opening into said chamber for optically viewing said particle through said optical sensor, a second window for admitting a beam of electromagnetic radiation for heating said particle in said chamber, and particle support means in said chamber;
a source of visible light and a conductor for providing a focused beam of said light into said chamber for targeting said particle to be aligned with a focal axis and in said focal plane when viewed by said optical sensor; and
a source of electromagnetic radiation and a conductor for providing a focused beam of said radiation through said second window and into said chamber for heating said particle, said source of light and said source of radiation being operably mounted on a movable support for adjusting the position of said light and said radiation beams with respect to said particle support means.

2. The apparatus set forth in claim 1 including:
a heating element interposed between said housing and said stage and operable to heat said housing to provide a predetermined temperature in said chamber.

3. The apparatus set forth in claim 2 including:
a heat sink interposed between said housing and said heating element and supporting said housing on said heating element and operable to maintain said housing at a substantially uniform temperature during operation of said apparatus.

4. The apparatus set forth in claim 1 including:
stops associated with said stage for limiting the movement of said stage in at least two directions to limit the movement of said housing with respect to said focal axis and a centerline for directing said light and said radiation beams toward said chamber.

5. The apparatus set forth in claim 1 wherein:
said housing includes a removable cover for closing said chamber, and said particle support means comprises a member connected to said cover and removable from said chamber upon removal of said cover from said housing.

6. The apparatus set forth in claim 1 wherein:
said housing includes a removable cover for closing said chamber and said particle support means comprises a member supported by said housing in said chamber independent of said cover.

7. The apparatus set forth in claim 1 wherein:
said housing includes a first passage for admitting a transport gas into said chamber and a second passage spaced from and above said first passage for conducting said transport gas and a pyrolyzate of said particle from said chamber to the exterior of said housing.

8. The apparatus set forth in claim 1 wherein:

said source of light and said source of radiation comprise separate laser devices supported for directing a beam of light and a beam of electromagnetic radiation into said chamber, said devices being mounted on said movable support for moving said devices to maintain the centerline of said light and said radiation beams in a predetermined position with respect to said housing, said movable support being operable to move said devices in at least two mutually perpendicular directions of movement.

9. The apparatus set forth in claim 8 wherein:
said movable support comprises three slide positioners interconnected in such a way to provide for positioning said light and said radiation sources along three mutually perpendicular axes.

10. The apparatus set forth in claim 8 wherein:
said apparatus includes beam reflecting mirrors and beam guide and shield means for guiding said light beam and said radiation beam along a predetermined common beam path to said chamber.

11. The apparatus set forth in claim 10 including:
a focusing lens interposed in said beam path between said chamber and said laser devices for focusing at least one of said light and said radiation beams to concentrate said beam to a predetermined maximum at said particle, said focusing lens being mounted on a beam guide member which is movable relative to said beam guide means and is supported on said movable support.

12. The apparatus set forth in claim 11 including:
a beam restrictor interposed between said focusing lens and said housing for restricting the intensity of said radiation beam.

13. The apparatus set forth in claim 11 including:
a movable mirror operable to intersect a beam path of said radiation beam and interposed in a beam path of said light beam for deflecting said light beam to be directed along said common beam path.

14. The apparatus set forth in claim 10 wherein:
said laser devices include beam emitting ends which are directed opposite the direction of said common beam path and said centerline and said apparatus includes plural beam reflecting mirrors interposed in said common beam path for redirecting said light and said radiation beams in a direction opposite to that which said light and said radiation beams emit from said laser devices, respectively.

15. An apparatus for generating a pyrolyzate of a microscopic particle for analysis comprising:
an optical sensor having a focal plane and a support stage;
a housing supported on said stage and including a closable chamber, window means opening into said chamber for optically viewing said particle through said optical sensor and for admitting a beam of electromagnetic radiation for heating said particle in said chamber, and a support in said chamber for supporting said particle;
a first laser device for emitting visible light and means for conducting a focused beam of a light along a beam path into said chamber for targeting said particle;
a second laser device for emitting electromagnetic radiation and means for conducting a focused beam of said radiation along said beam path into said chamber for heating said particle;
said laser devices include beam emitting ends which are directed opposite the direction of said beam path and said apparatus includes plural beam reflecting mirrors interposed in said beam path for redirecting said light and said radiation beams in a direction opposite to that which said beams light and said radiation emit from said laser devices, respectively, and along said beam path.

16. The apparatus set forth in claim 15 wherein:
said laser devices are mounted on a support for moving said devices to maintain the centerline of said light and said radiation beams in a predetermined position with respect to said housing, said support being operable to move said devices in at least two mutually perpendicular directions of movement.

17. The apparatus set forth in claim 16 wherein:
said support comprises three slide positioners interconnected in such a way to provide for positioning said laser devices along three mutually perpendicular axes.

18. The apparatus set forth in claim 15 wherein:
said apparatus includes beam reflecting means and beam guide and shield means for guiding said light beam and said radiation beam along said beam path to said chamber.

19. An apparatus for generating a pyrolyzate of analyzing a microscopic particle for analysis comprising:
an optical sensor having a focal plane and a movable support stage;
a housing supported on said stage and including a closable chamber, window means opening into said chamber for optically viewing said particle through said optical sensor, and for admitting a beam of electromagnetic radiation for heating said particle in said chamber;
a source of visible light and means for conducting a focused beam of said light into said chamber for targeting said particle to be aligned with said focal plane when viewed by said optical sensor;
a source of electromagnetic radiation and means for conducting a focused beam of said radiation through said window means and into said chamber for heating said particle, said source of light and said source of radiation being operably mounted on support means for adjusting the position of said light and said radiation beams with respect to a support member in said chamber; and
a stage movement limiter for limiting the movement of said stage in at least two directions to limit the movement of said housing with respect to said focal plane and a centerline for directing said light and said radiation beams toward said chamber.

* * * * *